United States Patent
Kiani (10) Patent No.: US 9,801,556 B2
(45) Date of Patent: *Oct. 31, 2017

(54) PATIENT MONITOR FOR MONITORING MICROCIRCULATION

(71) Applicant: Masimo Corporation, Irvine, CA (US)

(72) Inventor: Massi Joe E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/746,446

(22) Filed: Jun. 22, 2015

(65) Prior Publication Data

US 2015/0366472 A1    Dec. 24, 2015

Related U.S. Application Data

(63) Continuation of application No. 13/369,773, filed on Feb. 9, 2012, now Pat. No. 9,066,666.

(60) Provisional application No. 61/446,969, filed on Feb. 25, 2011.

(51) Int. Cl.
  *A61B 5/1455* (2006.01)
  *A61B 5/026* (2006.01)

(52) U.S. Cl.
  CPC ........ *A61B 5/0261* (2013.01); *A61B 5/14551* (2013.01)

(58) Field of Classification Search
  None
  See application file for complete search history.

(56) References Cited

U.S. PATENT DOCUMENTS

| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |

(Continued)

OTHER PUBLICATIONS

US 8,845,543, 09/2014, Diab et al. (withdrawn)

*Primary Examiner* — Eric Winakur
*Assistant Examiner* — Marjan Fardanesh
(74) *Attorney, Agent, or Firm* — Knobbe, Martens, Olson & Bear, LLP (57) ABSTRACT

A patient monitor capable of measuring microcirculation at a tissue site includes a light source, a beam splitter, a photodetector and a patient monitor. Light emitted from the light source is split into a reference arm and a sample arm. The light in the sample arm is directed at a tissue site, such as an eyelid. The reflected light from the tissue site is interfered with the light from the reference arm. The photodetector measures the interference of the light from both the sample arm and the reference arm. The patient monitor uses the measurements from the photodetector to calculate the oxygen saturation at the tissue site and monitor the microcirculation at the tissue site.

20 Claims, 5 Drawing Sheets

(56) References Cited

U.S. PATENT DOCUMENTS

| | | |
|---|---|---|
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |

(56) References Cited

U.S. PATENT DOCUMENTS

| | | |
|---|---|---|
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,338,447 B2 | 3/2008 | Phillips |
| 7,340,287 B2 | 3/2008 | Mason et al. |
| 7,341,559 B2 | 3/2008 | Schulz et al. |
| 7,341,562 B2 | 3/2008 | Pless et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Al-Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |

(56) References Cited

U.S. PATENT DOCUMENTS

| | | |
|---|---|---|
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,192,312 B2 | 11/2015 | Al-Ali |
| 2003/0069489 A1 | 4/2003 | Abreu |

(56) References Cited

U.S. PATENT DOCUMENTS

| | | |
|---|---|---|
| 2009/0143655 A1 | 6/2009 | Shani |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0261979 A1 | 10/2010 | Kiani |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |
| 2016/0113527 A1 | 4/2016 | Al-Ali |

PATIENT MONITOR FOR MONITORING MICROCIRCULATION

CROSS-REFERENCE TO RELATED APPLICATIONS

Any and all applications, for which a foreign or domestic priority claim is identified in the Application Data Sheet as filed with the present application, are hereby incorporated by reference. For example, this application is a continuation of U.S. patent application Ser. No. 13/369,773, filed Feb. 9, 2012, titled "Patient Monitor For Monitoring Microcirculation," which claims the benefit of U.S. Provisional Patent Application No. 61/446,969, filed Feb. 25, 2011, entitled "Patient Monitor for Monitoring Microcirculation," the entirety of each of which is hereby incorporated herein by reference to be considered a part of this specification.

FIELD

The present disclosure relates to medical sensors and specifically to a medical sensor and/or monitor for determining the circulation state in blood vessels.

BACKGROUND OF THE DISCLOSURE

Patient monitoring of various physiological parameters of a patient is important to a wide range of medical applications. Oximetry is one of the techniques that has developed to accomplish the monitoring of some of these physiological characteristics. It was developed to study and to measure, among other things, the oxygen status of blood. Pulse oximetry—a noninvasive, widely accepted form of oximetry—relies on a sensor attached externally to a patient to output signals indicative of various physiological parameters, such as a patient's constituents and/or analytes, including for example a percent value for arterial oxygen saturation, carbon monoxide saturation, methemoglobin saturation, fractional saturations, total hematocrit, billirubins, perfusion quality, or the like. A pulse oximetry system generally includes a patient monitor, a communications medium such as a cable, and/or a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation (SpO2) and/or pulse rate. The detector signal can also be used by the monitor to create an image on a display screen of the tissue being monitored.

High fidelity pulse oximeters capable of reading through motion induced noise are disclosed in U.S. Pat. Nos. 7,096,054, 6,813,511, 6,792,300, 6,770,028, 6,658,276, 6,157,850, 6,002,952 5,769,785, and 5,758,644, which are assigned to Masimo Corporation of Irvine, Calif. ("Masimo Corp.") and are incorporated by reference herein. Advanced physiological monitoring systems can incorporate pulse oximetry in addition to advanced features for the calculation and display of other blood parameters, such as carboxyhemoglobin (HbCO), methemoglobin (HbMet), total hemoglobin (Hbt), total Hematocrit (Hct), oxygen concentrations, glucose concentrations, blood pressure, electrocardiogram data, temperature, and/or respiratory rate as a few examples. Typically, the physiological monitoring system provides a numerical readout of and/or waveform of the measured parameter. Advanced physiological monitors and multiple wavelength optical sensors capable of measuring parameters in addition to SpO2, such as HbCO, HbMet and/or Hbt are described in at least U.S. Pat. No. 7,764,982, and U.S. application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and optical sensors including Rainbow™ adhesive and reusable sensors and RAD-57™ and Radical-7™ monitors capable of measuring SpO2, pulse rate, perfusion index (PI), signal quality (SiQ), pulse variability index (PVI), HbCO and/or HbMet, among other parameters, are also commercially available from Masimo Corp.

During blood circulation, arteries carry blood away from the heart in high volume and under high pressure. Arteries branch off into smaller blood vessels, called arterioles. Arterioles are well innervated, surrounded by smooth muscle cells, and are about 10-100 μm in diameter. Arterioles carry the blood to the capillaries, which are the smallest blood vessels, which are not innervated, have no smooth muscle, and are about 5-8 μm in diameter. Blood flows out of the capillaries into the venules, which have little smooth muscle and are about 10-200 μm in diameter. The blood flows from venules into the veins, which carry blood back to the heart. Arterioles, venules, and/or capillaries may also be referred to as microvessels.

Microcirculation generally refers to the vascular network lying between the arterioles and the venules, including the capillaries, as well as the flow of blood through this network. These small vessels can be found in the vasculature which are embedded within organs and are responsible for the distribution of blood within tissues as opposed to larger vessels in the macrocirculation which transport blood to and from the organs. One of the functions of microcirculation is to deliver oxygen and other nutrients to tissue. Sometimes, microcirculation in these small vessels can become blocked, interfering with the delivery of oxygen to the tissue.

SUMMARY

As placement of a physiological monitoring sensor is typically at a sensor site located at an extremity of the body, the state of microcirculation, such as whether vessels are blocked or open, can have a significant effect on the readings at the sensor site. It is therefore desirable to provide a patient monitor and/or physiological monitoring sensor capable of distinguishing the microcirculation state of blood vessels. In some embodiments, the patient monitor and/or sensor provide a warning and/or compensates a measurement based on the microcirculation state. In some embodiments, a microcirculation determination process implementable by the patient monitor and/or sensor is used to determine the state of microcirculation of the patient.

BRIEF DESCRIPTION OF THE DRAWINGS

Throughout the drawings, reference numbers may be re-used to indicate correspondence between referenced elements. The drawings are provided to illustrate embodiments of the disclosure described herein and not to limit the scope thereof.

DETAILED DESCRIPTION

Figure 1:
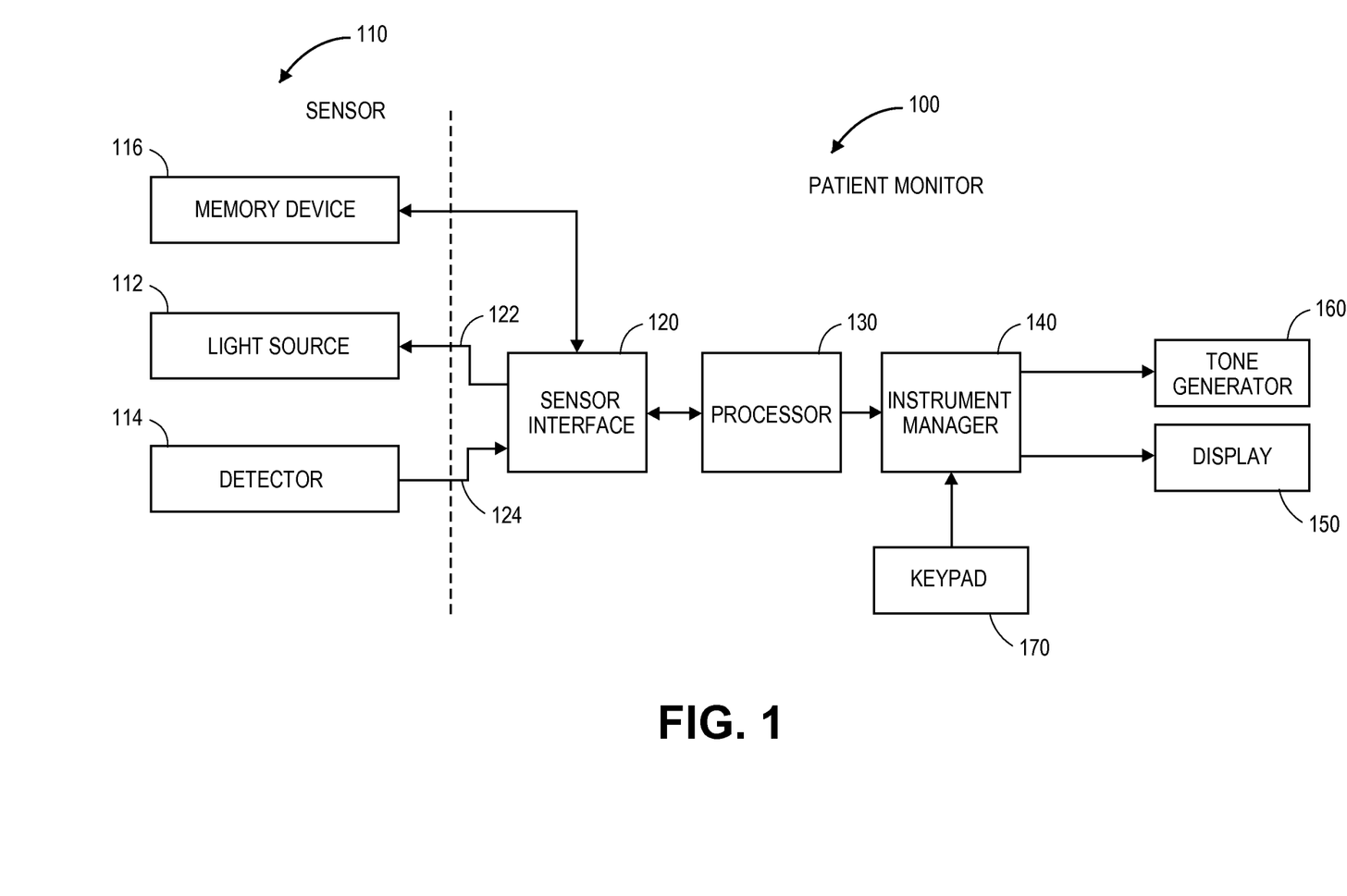
FIG. 1 illustrates a block diagram of a patient monitor, such as a pulse oximeter, and associated sensor.

FIG. 1 illustrates a block diagram of a patient monitor 100, such as a microcirculation monitoring device, and associated non-invasive sensor 110. Generally, in the case of a microcirculation monitoring device, the sensor 110 has a light source 112 and a photodiode detector 114. In one embodiment, the light source 112 includes two LED emitters, generally one at a red wavelength and one at an infrared wavelength. In another embodiment, the light source 112 includes one light emitter that emits light at multiple wavelengths and a collimator and spectral filter. The sensor 110 can be attached to a patient in a number of different locations including a finger, an ear, an arm, a leg, a toe, a cheek, a lip, a tongue, a forehead, or an eyelid.

Typically, non-invasive sensors are attached to a finger, ear, forehead or cheek or other extremity. However, these locations can have a number of drawbacks. For example, signals measured at the ear can be very weak compared to other sites. In addition, cold temperatures can lead to poor perfusion at the ear. In some instances, the signal may be so weak that a non-invasive measurement is not feasible.

A non-invasive sensor placed at the finger can also have a number of disadvantages. Similar, to the ear, cold temperatures, or a cold patient, may result in poor perfusion at the finger. In addition, a patient experiencing shock may experience poor perfusion in the finger, as blood is directed away from the extremities and to the body's core during shock. Patient movement can also make it difficult to obtain accurate non-invasive readings at the finger.

Despite the disadvantages of measuring at fingers and ears, measuring oxygen saturation and monitoring microcirculation at the eyelid has a number of advantages. For example, similar to other parts of the head, the eyelids are generally well perfused. In addition, lower temperatures are less likely to effect perfusion in the eyelid than in the ear or finger. Furthermore, there is less likely to be patient movement at the eyelid than at a finger, resulting in more accurate readings. In addition, placement of a sensor on the head during surgery can decrease the probability of a cable obstructing access to the patient. The thickness of the eyelid (approximately 1 mm) can also be of benefit when using Optical Coherence Tomography (OCT) devices.

For an eyelid, the sensor 110 is configured so that the light source 112 projects light into the microvessels of the eyelid. The light source 112 is activated by drive signals 122 from the patient monitor 100. The light entering the tissue is either absorbed, reflected, or refracted. After being reflected, some of the light returns in a direction that is substantially opposite from the direction it entered. The detector 114 is positioned in such a way so as to detect the reflected light as it emerges from the eyelid tissues. The detector 114 generates a signal 124, which is relayed by a cable or other means to the patient monitor 100.

In one embodiment, the patient monitor 100 can include a pulse oximeter to determine oxygen saturation (SpO2) by computing the differential absorption by arterial blood of the two wavelengths emitted by the LED emitters of the light source 112. Additional information regarding the use of a pulse oximeter can be found in U.S. application Ser. No. 13/101,093, entitled "Patient Monitor for Determining Microcirculation State," filed May 4, 2011, and U.S. Pat. No. 7,356,365, issued Apr. 8, 2008, entitled "Method and Apparatus for Tissue Oximetry," both of which are hereby incorporated by reference in their entirety. The patient monitor can further include a sensor interface 120, one or more processors 130, such as a microcirculation processor, an instrument manager 140, a display 150, an audible indicator (tone generator) 160, and a keypad 170. The sensor interface 120 provides a light source drive current 122 which drives the light source 112. The sensor interface 120 also has input circuitry for amplification and filtering of the signal 124 generated by the photodiode detector 114, which corresponds to the light detected from the tissue after having been reflected and/or refracted by the eyelid. The microcirculation processor 130 calculates microcirculation states of the microvessels in the eyelid tissue, as will be described in greater detail below, and can also calculate the oxygen saturation, as described in greater detail in U.S. application Ser. No. 13/101,093 and U.S. Pat. No. 7,356,365, previously incorporated by reference in their entirety. The instrument manager 140 provides hardware and software interfaces for managing the display 150, audible indicator 160, and keypad 170. The display 150 shows the computed oxygen saturation status, as described above, as well as the microcirculation status. The display 150 can also show an image of the microvessel. Similarly, other patient parameters including HbCO, HbMet, Hbt, Hct, oxygen concentrations, glucose concentrations, pulse rate, PI, SiQ, and/or PVI can be computed, as described in greater detail in U.S. application Ser. No. 13/101,093 and U.S. Pat. No. 7,356,365. The audible indicator 160 provides the pulse beep as well as alarms indicating desaturation and microcirculation events. The keypad 170 provides a user interface for such things as alarm thresholds, alarm enablement, and/or display options.

Computation of SpO2 relies on the differential light absorption of oxygenated hemoglobin, $HbO_2$, and deoxygenated hemoglobin, Hb, to determine their respective concentrations in the arterial blood. Specifically, pulse oximetry measurements are made at red (R) and infrared (IR) wavelengths chosen such that deoxygenated hemoglobin absorbs more red light than oxygenated hemoglobin, and, conversely, oxygenated hemoglobin absorbs more infrared light than deoxygenated hemoglobin, for example 660 nm (R) and 905 nm (IR).

To distinguish between tissue absorption at the two wavelengths, in some embodiments, the red and infrared emitters of the light source 112 are provided drive current 122 so that only one is emitting light at a given time. For example, the emitters can be cycled on and off alternately, in sequence, with each only active for a quarter cycle and with a quarter cycle separating the active times. This allows for separation of red and infrared signals and removal of ambient light levels by downstream signal processing. Because only a single detector 114 is used, it responds to both the red and infrared emitted light and generates a time-division-multiplexed ("modulated") output signal 124. This modulated signal 124 is coupled to the input of the sensor interface 120.

In addition to the differential absorption of hemoglobin derivatives, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site might also comprise skin, muscle, bone, venous blood, fat, pigment, and/or the like, each of which absorbs light. It is assumed that the background absorption due to these surrounding tissues is invariant and can be ignored. Thus, blood oxygen saturation measurements are based upon a ratio of the time-varying or AC portion of the detected red and infrared signals with respect to the time-invariant or DC portion: $R/IR=(Red_{AC}/Red_{DC})/(IR_{AC}/IR_{DC})$.

The desired SpO2 measurement is then computed from this ratio. The relationship between R/IR and SpO2 can be determined by statistical regression of experimental measurements obtained from human volunteers and calibrated measurements of oxygen saturation. In a pulse oximeter device, this empirical relationship can be stored as a "calibration curve" in a read-only memory (ROM) look-up table so that SpO2 can be directly read-out of the memory in response to input R/IR measurements.

The patient monitor 100 can also measure perfusion index, PI, which is a numerical value that indicates the strength of the IR signal returned from a monitoring site and provides a relative assessment of the pulse strength at the monitoring site. The perfusion index can be defined as follows: $PI=(IR_{max}-IR_{min})/IR_{DC}$, where $IR_{max}$ is the maximum value, $IR_{min}$ is the minimum value, and $IR_{DC}$ is the average value of the invariant portion. As the light absorption characteristic of blood is typically "flatter" or less sensitive to oxygen saturation around the infrared wavelength, the infrared signal from a sensor is influenced primarily by the amount of the blood at the monitoring site, not by the level of oxygenation in the blood. Accordingly, the perfusion index, which is a numerical value that indicates the strength of the IR signal returned from a monitoring site, provides a relative assessment of the pulse strength at the monitoring site. PI values generally range from 0.02% (very weak pulse strength) to 20% (very strong pulse strength). In some embodiments, PI can be measured using other wavelengths. For example, red, near red, near IR, as well as other wavelengths can be used.

In an embodiment, the sensor 110 also includes a memory device 116. The memory 116 can include any one or more of a wide variety of memory devices known to an artisan from the disclosure herein, including erasable programmable read-only memory (EPROM), electrically erasable programmable read-only memory (EEPROM), flash memory, other non-volatile memory, a combination of the same, or the like. The memory 116 can include a read-only device such as read-only memory (ROM), a read and write device such as random-access memory (RAM), combinations of the same, or the like. The remainder of the present disclosure will refer to such combination as simply EPROM for ease of disclosure; however, an artisan will recognize from the disclosure herein that the memory can include the ROM, the RAM, single wire memory, other types of memory, combinations of the same, or the like.

The memory device can advantageously store some or all of a wide variety data and information, including, for example, information on the type or operation of the sensor, type of patient or body tissue, buyer or manufacturer information, sensor characteristics including the number of wavelengths capable of being emitted, emitter specifications, emitter drive requirements, demodulation data, calculation mode data, calibration data, software such as scripts, executable code, or the like, sensor electronic elements, sensor life data indicating whether some or all sensor components have expired and should be replaced, encryption information, monitor or algorithm upgrade instructions or data, or the like. In an embodiment, the memory device can also include oxygen saturation to perfusion index and R/IR ratio to perfusion index ratios and/or data.

In certain situations, pulse oximetry sensors may produce anomalous readings, such as when a patient suffers from cyanosis. In a patient suffering from cyanosis, blood cells are uncharacteristically low on oxygen, leading to oxygen deficiency and giving the patient's skin a bluish-hue. One potential cause is that the patient's body produces too much hemoglobin, making the blood "thicker" or slower flowing, making microvessels more prone to blockage. Thus, a "blocked" microcirculation state can indicate cyanosis.

A "blocked" microcirculation state can also indicate other medical conditions, such as sepsis, systemic inflammatory response syndrome (SIRS), or septicemia. Sepsis is a potentially deadly medical condition that is characterized by a whole-body inflammatory state (called SIRS) and the presence of a known or suspected infection. The body may develop this inflammatory response by the immune system to microbes in the blood, urine, lungs, skin, or other tissue. Septicemia is a related medical term referring to the presence of pathogenic organisms in the bloodstream, which can lead to sepsis. Sepsis can also be referred to as blood poisoning. During sepsis or SIRS, inflammation in the body can cause constriction in blood vessels, leading to low blood pressure or insufficient blood flow.

During a "blocked" microcirculation state, blood cells can get blocked in the microvessels, such as the arterioles and capillaries. Blood cells can clump together or otherwise catch against the wall of blood vessels, creating a blockage that prevents blood cells, including red blood cells carrying hemoglobin, from passing through the blockage. However, plasma, which is composed of mostly water and in which the blood cells are suspended, is generally able to flow through passages in the blockage. In some situations, some blood vessels at the monitoring site may continue to have normal flow while some vessels are blocked. Thus, a "blocked" microcirculation state can indicate that some microvessels in an area are blocked and not necessarily all vessels in the area are blocked.

With the blockage preventing most or all the red blood cells from passing a blood vessel, at most only a limited amount of hemoglobin passes through a blocked blood vessel. In some situations, the blood vessel may only be partially blocked, where some hemoglobin passes through but less than when the blood vessel is unblocked. Normally, blood is made up of about 40-50% of red blood cells, of which about 95% is hemoglobin. Plasma, which is about 95% water, normally constitutes about 55% of the blood's volume.

Accordingly, a pulse oximeter sensor placed on a tissue site experiencing blockage in microcirculation vessels may detect mostly plasma passing through with no or only a small percentage of red blood cells, at least at part of the monitoring site. The resulting change in the normal composition of blood can cause anomalous readings in the patient monitor. As plasma has generally different absorption characteristics for red and infrared wavelengths than normal blood, pulse oximetry readings may become skewed. $Red_{AC}$ and/or $IR_{AC}$ can be affected, causing measured R/IR ratio to change. For example, if $Red_{AC}$ rises or $IR_{AC}$ drops, the R/IR ratio increases. Alternatively, if $Red_{AC}$ drops or $IR_{AC}$ rises, the R/IR ratio decreases. Thus, the value of R/IR can change due to a change in the light absorption of blood even if the underlying oxygen saturation of the blood remains the same.

However, by comparing oxygen saturation and PI for normal microcirculation to the oxygen saturation and PI for blocked microcirculation, such as by calculating and comparing ratios, the monitor can determine the existence of an abnormal situation. Typically, SpO2 is mostly independent of PI, with SpO2 varying minimally as PI increases. However, SpO2 varying by more than normal as PI increases can indicate an anomalous microcirculation state, such as a blockage. In one embodiment, by analyzing the measured ratios, the patient monitor 100 can determine the microcirculation state, such as whether a blocked vessel exists in the microvessels. Alternatively, multiple measurements of movement through the microvessels, such as the capillaries, can be used to determine the microcirculation state. For example, detected movement that is slower than normal can indicate blockage.

Figure 2A:
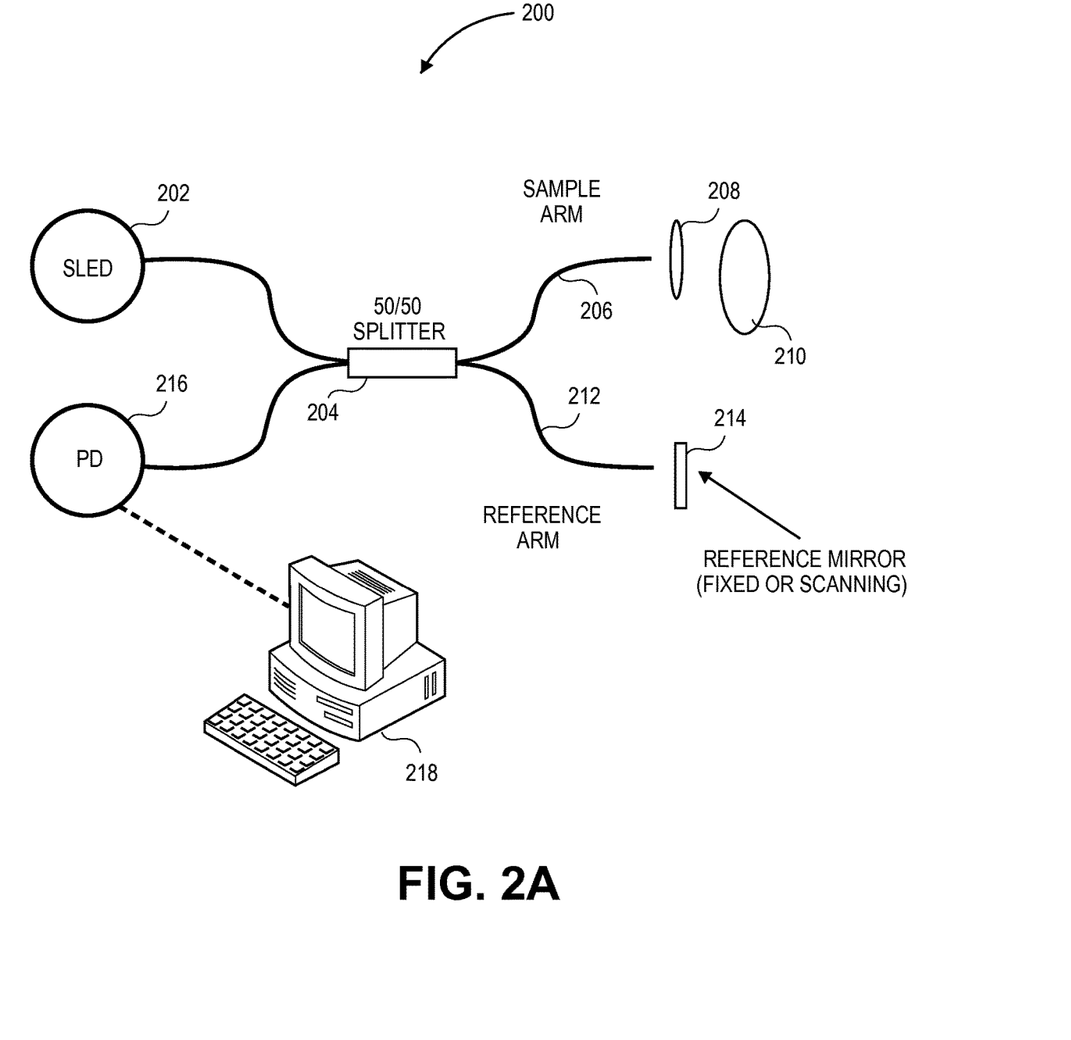
FIG. 2A is a schematic block diagram of a microcirculation monitoring device

FIG. 2A is a schematic block diagram of a microcirculation monitoring device 200, which is described in greater detail in U.S. Pat. No. 7,356,365, previously incorporated by reference. The monitoring device 200 includes a light source 202, beam splitter 204, sample arm 206, imaging optics 208 in close proximity to the tissue 210, a reference arm 212, a reflector 214, a photodetector 216 and a patient monitor 218.

As described in greater detail in U.S. Pat. No. 7,356,365, the light source 202 can emit light having an approximately equal wavelength, a spectrum of wavelengths, or a few different wavelengths, e.g., two. The wavelengths can be selected based on the absorption spectrum of oxygenated hemoglobin and deoxygenated hemoglobin. For example, peak absorption for a oxygenated hemoglobin is approximately 940 nm and peak absorption for a deoxygenated hemoglobin is approximately 660 nm. Thus, wavelengths of 660 nm and 940 nm can be used. The light from the light source 202 is split by a beam splitter 204 between a sample arm 206 and a reference arm 212. Reflected signals from arms 206 and 212 interfere and are presented to photodetector 216 for measurement. Preferably, the end of the sample arm 206 can contain imaging optics 208 to tailor the spot size according to the tissue being measured. The imaging optics 208 can provide high coupling efficiency between the optical system and the tissue.

The tissue volume with which the light interacts (referred to as the interaction volume) is determined by the spot size of the imaging optics (surface area) and the coherence length of the light (depth). Reference arm 212 of the interferometer determines the phase shift applied to the reference beam which in turn determines which reflected light from the sample will constructively interfere with the shifted reference beam. Thus, the reference arm 212 determines the depth within the interaction volume from which scattered light is measured. The sample arm 206 can have either a fixed or scanning reflector 214 (such as a mirror). This can allow for a fixed sensor depth, adjustable sensor depth, or scan of multiple depths within the tissue.

The photodetector 216 measures the interference of the light from both the sample arm 206 and the reference arm 212. The patient monitor 218 uses the measured constructively interfered light at the different wavelengths to provide a measurement of the oxygen saturation, PI, and to monitor the microcirculation. Microcirculation measurements can also be calculated by obtaining multiple images of the tissue site and analyzing the movement of blood cells between the images.

Figure 2B:
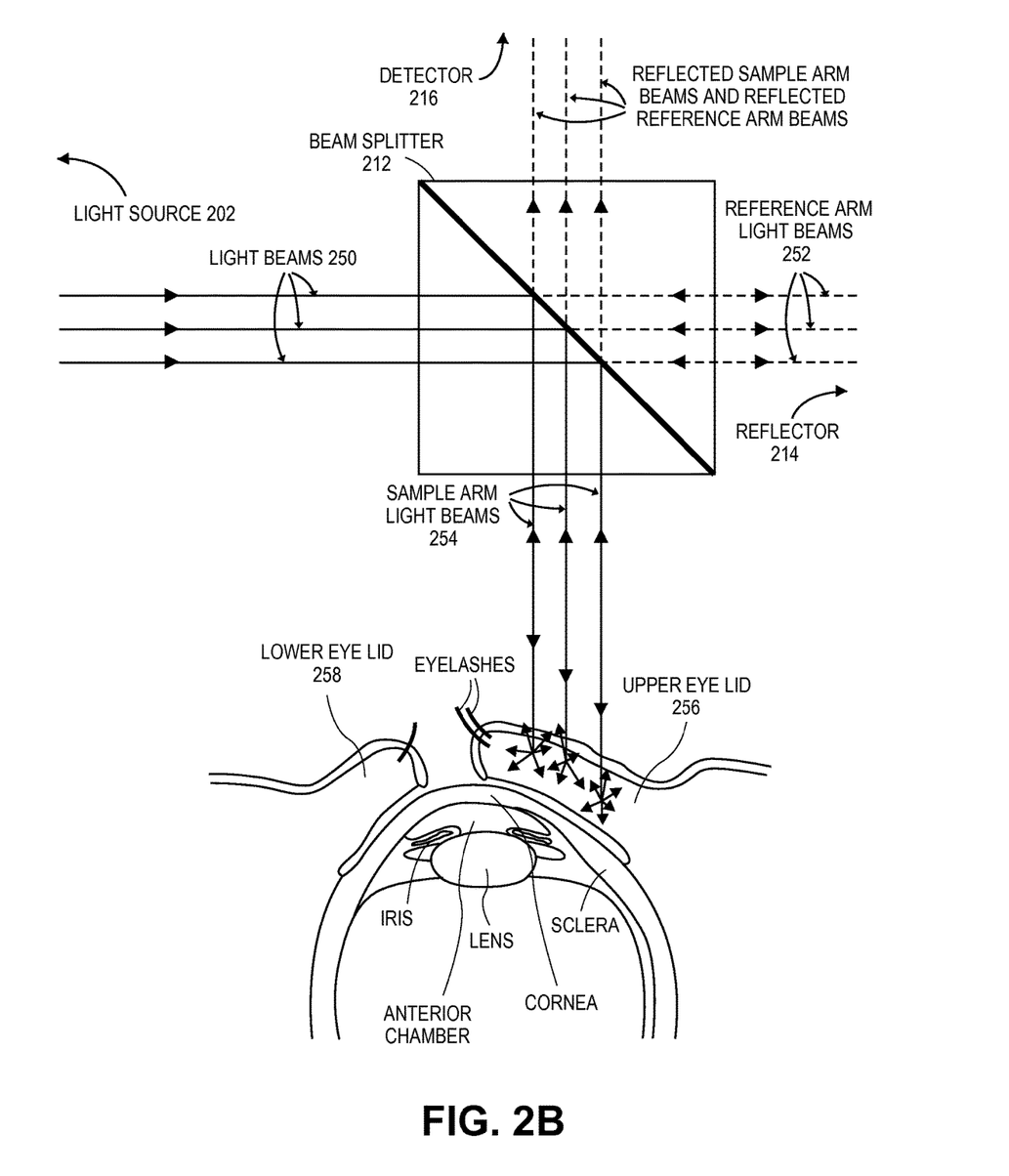
FIG. 2B is a block illustrating an eyelid being monitored by a microcirculation monitoring device.

FIG. 2B illustrates a block drawing of an eyelid being monitored by a microcirculation monitoring device 200. As illustrated, light beams 250 from a light source 202 (FIG. 2A) are split using the beam splitter 204 into reference arm light beams 252 and sample arm light beams 254. After the light beams 250 are split, the reference arm light beams 252 travel down the reference arm 212 (FIG. 2A) to interact with the reflector 214 (FIG. 2A), and the sample arm light beams 254 travel down the sample arm 206 (FIG. 2A) to interact with the tissue from the upper eyelid 256. Although illustrated as interacting with the upper eyelid 256, it is to be understood that the lower eyelid 258 can also be used.

The upper eyelid 256 either absorbs, reflects and/or refracts the sample arm light beams 254. Some of the sample arm light beams 254 are reflected back to the beam splitter 212. The beam splitter 212 directs at least some of the reflected sample arm light beams 254 to the detector 216 (FIG. 2A).

The light beams traveling down the reference arm 212 (FIG. 2A) interact with a reflector 214 (FIG. 2A) and are reflected back to the beam splitter 212. Similar to the reflected sample arm light beams 254, the reflected reference arm light beams 256 are also directed to the detector 216 by the beam splitter 212. As discussed above, a patient monitor 200 (FIG. 2A) uses the detected signals obtained from the interference of the reflected sample arm light beams 254 and the reflected reference arm light beams 252 to calculate oxygen saturation, perfusion index and other physiological parameters. The patient monitor 200 (FIG. 2A) can also use the signals obtained from the detector 216 to monitor microcirculation in the eyelid. The microcirculation states can be monitored by comparing ratios of oxygen saturation and PI, as described in greater detail below, or comparing images obtained of the microvessels, as described above. If the microcirculation falls below a predetermined threshold, an alarm can be activated.

Although not illustrated in FIG. 2B, imaging optics 208 can also be used to focus the sample arm light beams 254 prior to interacting with the eyelids. Furthermore, the end of the sample arm 206 and imaging optics 208 can be placed in close proximity to the eyelid. In an embodiment, when a patient is unconscious, such as during a surgery, the end of the sample arm 206 and imaging optics 208 can be secured to the patient using an adhesive. The adhesive can attach to the patient's face, such as the cheek, forehead, ear or nose. Alternatively, the end of the sample arm 206 and imaging optics 208 can be fixedly attached to a pair of glasses or other device configured to cover a patient's eyes. The glasses or other device can be placed on the patient such that the sample arm light beams 254 interact with the eyelid tissue. The glasses or other placement device can be specially configured to ensure that the proper distance between the eyelid and the sample arm 206 and imaging optics 208 is achieved. The reference arm 212 and reflector 214 are configured and appropriate wavelength and polarization selected such that the appropriate depth of the eyelid tissue is measured.

Alternative designs can be used to monitor the microcirculation in an eyelid. For example, multiple images of a microvessel can be used to monitor the microcirculation. The images can be obtained using Optical Coherence Tomography (OCT), as is well known in the art. One method of obtaining images of microvessels is described in greater detail in U.S. application Ser. No. 11/524,866, entitled "Microcirculation Imaging." For example, a light source can output a beam of light having a broad spectrum of wavelengths. The beam of light can be collimated and pass through a spectral filter, and a beam splitter can split the light such that a beam of light having approximately one wavelength is directed towards microvessels of the eyelid. The light can be either polarized or non-polarized. A polarizer located on one edge of the beam splitter can polarize the light linearly, elliptically, or circularly, as desired. The wavelength and polarization of the light can be selected based on the desired measurement depth. The wavelength and polarization of the light can be altered using the spectral filter and/or polarizer. In one embodiment, the wavelength can be between 420 and 810 nm. In another embodiment, the wavelength can be in the light green spectrum (525-575 nm). The reflected light from the eyelid can be collected using a converging lens and a photodetector. A processor can use the signals from the photodetector to render an image of the eyelid tissue, or microvessels. Multiple images of the microvessels can be used to calculate the velocity of the microcirculation and detect blockage. For example, the distance traveled by the blood cells between measurements can be compared with the time between measurements to calculate velocity. If the velocity is below a certain threshold an alarm can be activated.

Other OCT methods can also be used to obtain images of the microvessels of the eyelid or other tissue. For example, multiple light emitters emitting different wavelengths of light can be used to obtain an image. Multiple images of the eyelid tissue can then be used by a patient monitor to calculate the velocity of the blood passing through the tissue, thereby monitoring the microcirculation of the eyelid.

Figure 3:
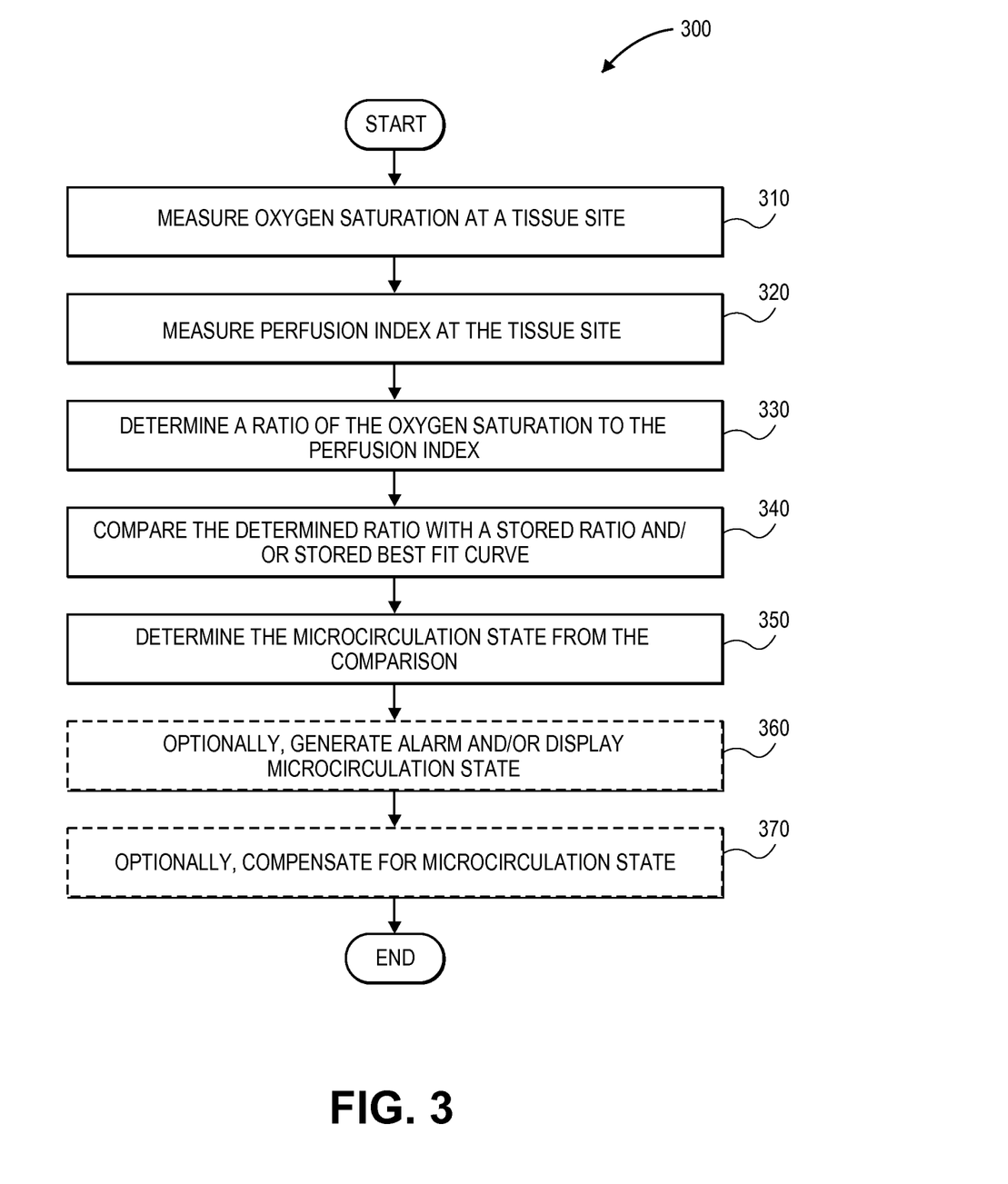
FIG. 3 illustrates a flow diagram for a process for determining the state of microcirculation usable by a pulse oximeter.

FIG. 3 illustrates a flow diagram for a process 300 for determining the state of microcirculation usable by a pulse oximeter. Microcirculation state can be determined by comparison with microcirculation data stored on a patient monitor, such as the patient monitor 100 of FIG. 1. The process 300 can be implemented by embodiments of the sensor 110 and/or patient monitor 100 of FIG. 1 or other suitable device.

While in conventional pulse oximetry, measurements are generally taken pulse-by-pulse and averaged over pulses, microcirculation measurements can be measured using only a single pulse or a portion of a single pulse. This can be done, for example, at the minimum and/or maximum blood flow of a pulse. Microcirculation measurements can also be determined over multiple pulses. In some embodiments, microcirculation measurements are taken during a portion of the normal measurement time used by a physiological sensor to take a measurement of a parameter, thereby allowing detection of aberrant parameter measurements using the microcirculation measurements. For example, while a pulse oximeter is measuring SpO2 over several pulses, microcirculation measurements can be taken per pulse and a warning given if an irregular microcirculation state is detected, thereby notifying a user of a possible aberration in the current SpO2 reading.

At block 310, oxygen saturation is measured at a tissue monitoring site. In one embodiment, oxygen saturation is determined using a pulse oximeter sensor.

At block 320, perfusion index or pulse strength is measured. In one embodiment, the perfusion index is determined using the same sensor used to measure oxygen saturation so that readings are taken at the same monitoring site.

At block 330, a ratio of oxygen saturation to perfusion index is determined. Oxygen saturation can be a SpO2 value based on the measured R/IR ratio looked-up against a calibration curve. Alternatively, the ratio can be perfusion index to oxygen saturation. In other embodiments, the measured R/IR ratio can be used directly instead of SpO2.

In some embodiments, multiple readings of perfusion index and oxygen saturation can be taken and averaged together before determining the ratio in order to account for outliers. The multiple readings can be filtered before averaging. For example, readings can first be filtered based on closeness of PI values before the readings are averaged together.

At block 340, the determined ratio in block 330 is compared to stored microcirculation data. The stored data can be data sets for microcirculation states. In some embodiments, a ratio, a curve, a line, table, data points, or formula can be stored that corresponds to a data set. The measured perfusion index and oxygen saturation can then be compared to the stored data. In some embodiments, multiple readings are taken and a best fit line or curve is generated and compared to a stored best fit line or curve. In some embodiments, readings are collected at various PI values in order to generate a trend line.

At block 350, the microcirculation state is determined from comparison of the stored microcirculation data. For example, if the determined ratio is similar to a stored ratio corresponding to a data set for unblocked microcirculation, the microcirculation state is determined to be unblocked. Other data sets for other microcirculation states, such as blocked and/or partially blocked can also be stored. Where multiple data sets are stored, the state can be determined by selecting the state corresponding to the stored ratio closest to the measured ratio.

At block 360, the monitor can optionally generate an alarm and/or display the microcirculation state. For example, an alarm signal and/or icon can be generated by the monitor to indicate that the readings may be anomalous, such as when a blocked or partially blocked microcirculation state is detected. The alarm can be a visual indicator (e.g., icon, message or image) and/or an audio indicator. In an embodiment, the alarm can indicate the detection of cyanosis, sepsis, SIRS or other medical condition based at least partly on the determined microcirculation state. In some embodiments, no action is taken, such as when readings are determined to be normal or non-threatening.

At block 370, the monitor can optionally compensate for the microcirculation state in order to improve accuracy of the readings. After the microcirculation state returns to normal, the compensation process can be ended.

In one embodiment, an offset can be added to the measured parameter value, such as SpO2. The offset can be calculated based on data sets for microcirculation state. Different microcirculation states can have different offsets. For example, if a "blocked" microcirculation state produces high readings for low PI values, a negative offset can be used. However, if a "blocked" state produces a low value for high PI values, then a positive offset can be used. In one embodiment, a varying offset can be used depending on the value of PI.

In one embodiment, a different wavelength emitter can be used to compensate for a microcirculation state. For example, rather than using a regular infrared emitter, typically 905 nm, an emitter with a different infrared wavelength, such as 970 nm can be used. In one embodiment, the different wavelength is selected such that the wavelength is at a "flat" section of the light absorption curve for plasma, that is, where the light absorption is not much affected by changes in oxygen saturation, as described in greater detail in U.S. application Ser. No. 13/101,093. In one embodiment, the selected wavelength with regards to plasma mimics the properties of the regular wavelength with regards to normal flowing blood. In some embodiments, a different wavelength red emitter can be used instead of the regular red wavelength emitter.

In some embodiments, the pulse oximeter sensor used to measure oxygen saturation and PI can be provided with an additional emitter at a different wavelength than the existing emitters. When a certain microcirculation state is detected, such as a "blocked" state, the additional emitter can be used. For example, a pulse oximetry sensor can be equipped with LED's capable of emitting at 660 nm, 905 nm, and at 970 nm wavelengths. Under normal operation, the 660 nm and 905 nm emitters are active. However, upon detecting a blocked microcirculation state, the 905 nm emitter can be deactivated and the 970 nm emitter activated in its place. In some embodiments, a variable wavelength emitter can be used rather than separate emitters. In some embodiments, the additional emitter can be a red wavelength emitter.

Figure 4:
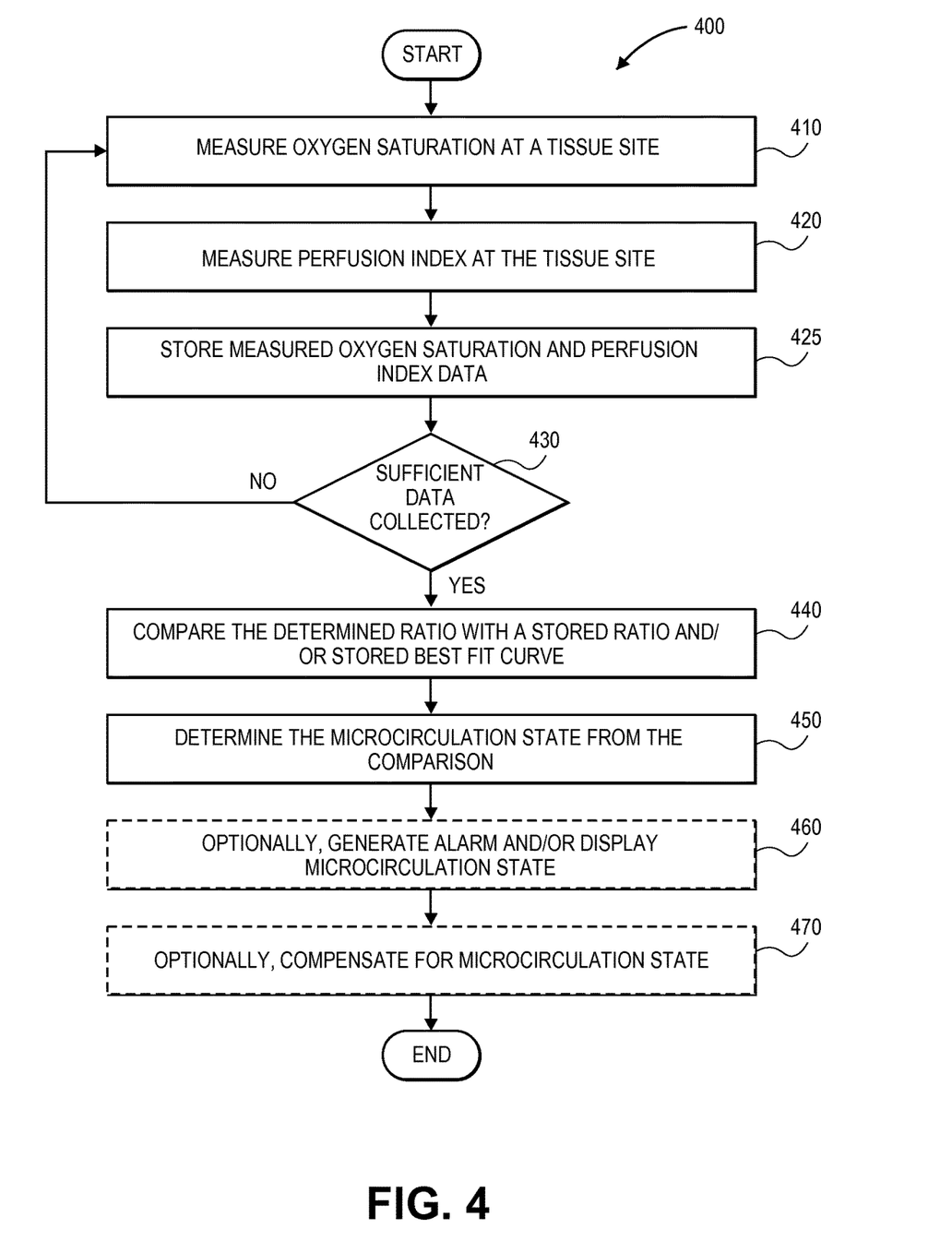
FIG. 4 illustrates a flow diagram for a process for determining the state of microcirculation wherein multiple data points are collected.

FIG. 4 illustrates a flow diagram for a process 400 for determining the state of microcirculation wherein multiple data points are collected. The process 400 can be implemented by embodiments of the sensor 110 and/or patient monitor 100 of FIG. 1 or other suitable device.

At block 410 and block 420, oxygen saturation and perfusion index are measured. At block 425, measured values are stored in memory. Each paired measurement forms a data point.

At block 430, the number of stored data points is checked to determine if sufficient data has been collected to determine the microcirculation state. Data can be sufficient if a set number of data points have been collected, a set amount of time has passed, and/or a spectrum of data points have been collected, such as for differing values of PI.

At block 440, the stored measured data is compared with stored microcirculation data. Typically, the microcirculation data is pre-stored on the pulse oximeter before use, as opposed to collected during use. A comparison can involve generating a curve or line from the measured data, calculating a rate of change for the stored data, generating a trend line for the measured data or the like and comparing with the stored microcirculation data.

At block 450, the microcirculation state is determined from comparison of the stored microcirculation data. For example, if the measured data is similar to microcirculation data corresponding to a data set for unblocked microcirculation, the microcirculation state is determined to be unblocked. Other data sets for other microcirculation states, such as for blocked and/or partially blocked can also be stored. Where multiple data sets are stored, the state can be determined by selecting the state corresponding to the stored ratio closest to the measured ratio.

Blocks 460 and 470 are similar to steps 360 and 370 described in FIG. 3.

As will be apparent from the above description, the R/IR ratio corresponds to oxygen saturation or SpO2 and can be used in place of oxygen saturation or SpO2 for the above comparisons, and vice versa.

While the above systems and methods have been described in terms of oxygen saturation and PI, other physiological parameters can be measured in place of or in addition to oxygen saturation and/or perfusion index and used to determine microcirculation state. For example, perfusion index is an indication of amplitude and/or signal strength and other parameters or measurements indicating amplitude and/or signal strength can be used. In some embodiments, one or more different sensors can be used in place of or in addition to a pulse oximeter sensor.

In another embodiment, the microcirculation state can be calculated without calculating oxygen saturation. For example, using OCT, as described above, multiple measurements of the movement of blood within the microvessels can be taken. The multiple measurements can then be compared to determine the velocity of the blood traveling through the microvessels. For example, the distance traveled by the blood between measurements can be compared with the time between measurements to calculate velocity. In one embodiment, images of the microvessels are used to measure the movement of blood in the microvessels.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Various systems and processes for determining microcirculation events have been disclosed in detail in connection with various embodiments. These embodiments are disclosed by way of examples only and are not to limit the scope of the claims that follow. Indeed, the novel methods and systems described herein can be embodied in a variety of other forms; furthermore, various omissions, substitutions and changes in the form of the methods and systems described herein can be made without departing from the spirit of the inventions disclosed herein. The claims and their equivalents are intended to cover such forms or modifications as would fall within the scope and spirit of certain of the inventions disclosed herein. One of ordinary skill in the art will appreciate the many variations, modifications and combinations. For example, the various embodiments of the microcirculation determination process can be used with oxygen saturation sensors and with both disposable and reusable sensors. In some embodiments, the determination process can be applied to other blood vessels to detect a blockage, even in vessels not involved in microcirculation.

Furthermore, in certain embodiments, the systems and methods described herein can advantageously be implemented using computer software, hardware, firmware, or any combination of software, hardware, and firmware. In one embodiment, the system includes a number of software modules that comprise computer executable code for performing the functions described herein. In certain embodiments, the computer-executable code is executed on one or more general purpose computers or processors. However, a skilled artisan will appreciate, in light of this disclosure, that any module that can be implemented using software can also be implemented using a different combination of hardware, software or firmware. For example, such a module can be implemented completely in hardware using a combination of integrated circuits. Alternatively or additionally, such a module can be implemented completely or partially using specialized computers or processors designed to perform the particular functions described herein rather than by general purpose computers or processors.

Moreover, certain embodiments of the invention are described with reference to methods, apparatus (systems) and computer program products that can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the acts specified herein to transform data from a first state to a second state.

Each of the processes, methods, and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A method for monitoring microcirculation of a patient at an eyelid, the method comprising:
receiving a plurality of signals corresponding to light detected by a sensor after having been reflected and/or refracted at a tissue site of an eyelid, wherein the light comprises at least a red beam having a red wavelength and an infrared (IR) beam having an infrared wavelength;
calculating oxygen saturation based at least in part on a ratio of a first signal of the plurality of signals that corresponds to the red beam with respect to a second signal of the plurality of signals that corresponds to the IR beam;
calculating a perfusion index based at least in part on a signal strength of at least one of the plurality of signals;
determining a ratio between the oxygen saturation and the perfusion index;
comparing the determined ratio with stored microcirculation data corresponding to one or more microcirculation states; and
determining a microcirculation state of at least a portion of blood vessels in the eyelid based at least in part on the comparison of the determined ratio with the stored microcirculation data.

2. The method of claim 1, wherein the microcirculation state is further determined using multiple images of the eyelid.

3. The method of claim 1, further comprising splitting the light into one or more sample arm beams of light and one or more reference arm beams of light, wherein at least one of the sample arm beams of light is directed towards the eyelid and the one or more reference arm beams of light is directed towards a reflector.

4. The method of claim 3, wherein the a microcirculation state is further based at least in part on an optical interference between reflected one or more reference arm beams of light and reflected one or more sample arm beams of light.

5. The method of claim 1, wherein the first signal comprises a ratio of a time-varying portion of the red beam with respect to a time-invariant portion of the red beam, and wherein the second signal comprises a ratio of a time-varying portion of the IR beam with respect to a time-invariant portion of the IR beam.

6. The method of claim 1, wherein the perfusion index is based at least in part on a signal strength of a particular signal of the plurality of signals, and wherein the perfusion index is calculated by dividing a difference between a maximum particular signal value and a minimum particular signal value by an average value of an invariant portion of the particular signal.

7. The method of claim 6, wherein the particular signal corresponds to a light beam having one of an IR wavelength, a red wavelength, or a near red wavelength.

8. The method of claim 1, further comprising compensating at least one of the perfusion index or the oxygen saturation based on the microcirculation state.

9. The method of claim 8, wherein compensating comprises at least one of adding an offset to the oxygen saturation or adding an offset to the perfusion index.

10. The method of claim 8, wherein compensating comprises adjusting a light source to emit another beam of light having a different wavelength than the wavelengths of the red beam and the IR beam, such that the light absorption at the different wavelength is not much affected by changes in oxygen saturation.

11. A microcirculation monitoring device configured to monitor the microcirculation of a patient at an eyelid, the monitoring device comprising:
a light source configured to emit light comprising a plurality of light beams, wherein the plurality of light beams comprises at least a red beam having a red wavelength and an infrared (IR) beam having a IR wavelength;
a detector configured to detect the light after having been reflected and/or refracted at a tissue site of an eyelid; and one or more processors in communication with the detector, the one or more processors configured to:

receive a plurality of signals corresponding to the light detected by the detector, the plurality of signals comprising at least a first signal that corresponds to the red beam and a second signal that corresponds to the IR beam, calculate an oxygen saturation based at least in part on a ratio of the first signal with respect to the second signal, calculate a perfusion index based at least in part on a signal strength of at least one of the plurality of signals, determine a ratio between the oxygen saturation and the perfusion index, compare the determined ratio with stored microcirculation data corresponding to one or more microcirculation states, and determine a microcirculation state of a least a portion of blood vessels in the eyelid based at least in part on the comparison of the determined ratio with the stored microcirculation.

12. The monitoring device of claim 11, wherein the one or more processors are further configured to determine the microcirculation state using multiple images of the eyelid.

13. The monitoring device of claim 11, further comprising a beam splitter configured to split at least some of the plurality of emitted light beams into one or more sample arm beams of light and one or more reference arm beams of light, wherein at least one of the sample arm beams of light is directed towards the eyelid and the one or more reference arm beams of light is directed towards a reflector.

14. The monitoring device of claim 13, wherein the microcirculation state is further based at least in part on an optical interference between reflected one or more reference arm beams of light and reflected one or more sample arm beams of light.

15. The monitoring device of claim 11, wherein the first signal comprises a ratio of a time-varying portion of the red beam with respect to a time-invariant portion of the red beam, and wherein the second signal comprises a ratio of a time-varying portion of the IR beam with respect to a time-invariant portion of the IR beam.

16. The monitoring device of claim 11, wherein the perfusion index is based at least in part on a signal strength of a particular signal of the plurality of signals, and wherein the perfusion index is calculated by dividing a difference between a maximum particular signal value and a minimum particular signal value by an average value of an invariant portion of the particular signal.

17. The monitoring device of claim 16 wherein the particular signal corresponds to a light beam having one of an IR wavelength, a red wavelength, or a near red wavelength.

18. The monitoring device of claim 11, wherein the one or more processors are further configured to compensate at least one of the perfusion index or the oxygen saturation based on the microcirculation state.

19. The monitoring device of claim 18, wherein compensating comprises adding an offset to the oxygen saturation or adding an offset to the perfusion index.

20. The monitoring device of claim 18, wherein compensating comprises adjusting the light source to emit another beam of light having a different wavelength than the wavelengths of the red beam and the IR beam, such that the light absorption at the different wavelength is not much affected by changes in oxygen saturation.

* * * * *